United States Patent
Kalkbrenner et al.

(10) Patent No.: US 9,091,857 B2
(45) Date of Patent: Jul. 28, 2015

(54) MICROSCOPE AND METHOD FOR THE MICROSCOPIC DETECTION OF LIGHT OF A SAMPLE

(75) Inventors: Thomas Kalkbrenner, Jena (DE); Ralf Wolleschensky, Jena (DE)

(73) Assignee: Carl Zeiss Microscopy GmbH, Jena (DE)

( * ) Notice: Subject to any disclaimer, the term of this patent is extended or adjusted under 35 U.S.C. 154(b) by 409 days.

(21) Appl. No.: 13/071,752

(22) Filed: Mar. 25, 2011

(65) Prior Publication Data

US 2012/0002030 A1    Jan. 5, 2012

(30) Foreign Application Priority Data

Mar. 26, 2010  (DE) .......................... 10 2010 013830

(51) Int. Cl.
  *G02B 21/16* (2006.01)
  *G01N 21/65* (2006.01)

(52) U.S. Cl.
  CPC ................ *G02B 21/16* (2013.01); *G01N 21/65* (2013.01); *G01N 2021/655* (2013.01)

(58) Field of Classification Search
  CPC .. G02B 21/00–21/368; G02B 26/00–26/0891; G02F 1/015–1/0159
  USPC .................................. 359/368–398, 237–324
  See application file for complete search history.

(56) References Cited

U.S. PATENT DOCUMENTS

| | | | | |
|---|---|---|---|---|
| 5,814,820 | A * | 9/1998 | Dong et al. ................. | 250/458.1 |
| 6,246,477 | B1 * | 6/2001 | Feldman ....................... | 356/340 |
| 6,496,267 | B1 * | 12/2002 | Takaoka ........................ | 356/497 |
| 6,911,646 | B1 * | 6/2005 | Weitekamp .................... | 250/234 |
| 2001/0045529 | A1 * | 11/2001 | Iketaki et al. .............. | 250/493.1 |
| 2002/0154317 | A1 * | 10/2002 | Kempe ........................... | 356/484 |
| 2005/0030548 | A1 * | 2/2005 | Li ............................... | 356/497 |
| 2006/0290924 | A1 * | 12/2006 | Iketaki et al. ................. | 356/300 |
| 2010/0060969 | A1 * | 3/2010 | Ando et al. .................... | 359/238 |
| 2010/0067102 | A1 * | 3/2010 | Yokoi et al. ................... | 359/385 |
| 2011/0310475 | A1 * | 12/2011 | Iketaki ......................... | 359/388 |
| 2012/0268812 | A1 * | 10/2012 | Anhut et al. .................. | 359/386 |
| 2013/0020473 | A1 * | 1/2013 | Kalkbrenner et al. ........ | 250/216 |

OTHER PUBLICATIONS

Chen, Nanguang et al., "Focal modulation microscopy" Nov. 10, 2008. Optics Express, vol. 16, No. 23, pp.*
Wong, Chee Howe et al., "Simple spatial phase modulator for focal modulation microscopy" Jun. 10, 2009. Applied Optics, vol. 48, No. 17, pp. 3237-3242. pp. 18764-18769.*

* cited by examiner

*Primary Examiner* — Stephone B Allen
*Assistant Examiner* — Jeffrey Madonna
(74) *Attorney, Agent, or Firm* — Duane Morris LLP

(57) ABSTRACT

A microscope or use of a microscope with at least one illumination beam that is phase-modulated along its cross section partially with a modulation frequency, in which an advantageously local excitation of a transition, advantageously a fluorescence excitation in a sample, is performed by means of a pump beam of a first wavelength and the transition is induced and detected advantageously by means of a second beam, advantageously of a second wavelength, or a local heating is generated that is read out from the detection signals by means of a detection unit, advantageously an infrared camera.

20 Claims, 4 Drawing Sheets

MICROSCOPE AND METHOD FOR THE MICROSCOPIC DETECTION OF LIGHT OF A SAMPLE

RELATED APPLICATIONS

The present application claims benefit of German Application No. DE 10 2010 013 830.4 filed on Mar. 26, 2010, the contents of which are incorporated by reference in their entirety.

FIELD OF THE INVENTION

The invention relates, in particular, to pump-probe microscopy in strongly scattering media with limited penetration depth, in particular, biological samples.

Known methods include:
Coherent pump-probe methods, see, e.g., Stimulated Raman Scattering or "SRS". See, e.g., Freudiger et al., Science 322, 1857 (2008) ("Freudiger")
Incoherent pump-probe method, such as, e.g., photothermal modulation microscopy. See, e.g., Boyer et al., Science 297, 1160 (2002) ("Boyer"), and Lasne et al., Optics Express 15, 14184 (2007) ("Lasne")

The problem of the strong background signal and the limited penetration depth in greatly scattering samples (tissue) also presents itself, in particular, in these so-called pump-probe experiments or arrangements. Here, normally energy is introduced into the system with the "pump" beam of a wavelength 1, wherein a certain transition (e.g., fluorescence excitation) is to be stimulated with this energy. With the "probe" beam of a wavelength 2 that could also be equal to the first wavelength, this transition is then either induced (e.g., SRS, see below) or read out (e.g., photothermal modulation microscopy, see below).

Examples of such pump-probe methods are:
Stimulated Raman Scattering (SRS). See, e.g., Freudiger.
Stimulated emission microscopy. See, e.g., Min et al., Nature 461, 1105 (2009) ("Min").
Photothermal modulation microscopy. See, e.g., Boyer and Lasne.

PRIOR ART

The present invention provides a solution to this problem, and relates to the surprising use of Focal Modulation Microscopy (FMM) for pump-probe microscopy. Focal Modulation Microscopy has been published. See, e.g., Chen et al, Opt. Express 16, 18764 (2008) ("Chen"); Wong et al., Appl. Opt. 48, 3237 (2009) ("Wong").

OBJECTS

A modulation of the pump beam or the probe beam is carried out as described in the following embodiments.

This modulation is transferred onto the probe beam (for modulation of the pump beam) or onto the pump beam for modulation of the "signal beam" (Stokes beam in SRS, Freudiger).

The modulation in the probe beam is measured, for example, according to Chen and Wong, above.

In FMM, advantageously half of the stimulation laser beam (in diameter) is phase-modulated. When focusing through a microscope objective, this half phase modulation leads to an intensity modulation in the focal volume. This intensity modulation can be detected after the confocal pinhole, for example, by lock-in detection. The advantage of the method consists in that only the ballistic, that is, non-scattered, photons contribute to this modulation signal; the photons that are scattered several times, e.g., in greatly scattering media, lose the fixed phase relationship.

The previously common methods of modulation of the pump beam by means of Electro-Optical Modulation (EOM) or Acousto-Optical Modulation (AOM) lead to an intensity modulation of the entire beam at each position in the sample. Accordingly, the lock-in detection of the modulated signal also extracts signal components from the entire beam path through the sample and not, for example, only from the focal range. Thus, the basic problems remain of undesired background signal in greatly scattering samples and high penetration depth in tissue, respectively.

In contrast, in the method/arrangement presented here, no amplitude modulation of the pump beam takes place.

The FMM phase modulation has the result that only the ballistic (non-scattered) photons keep their fixed phase relationship and thus only the focus of the pump beam experiences an amplitude modulation. Accordingly, a modulation of the probe beam that can then be detected with a lock-in method takes place only in the focal volume.

Applications, embodiments are summarized, but not limited to:
Coherent pump-probe methods,
Incoherent pump-probe methods,
Induced Raman scattering or Stimulated Raman Scattering (SRS) (see, e.g., Freudiger),
Photothermal modulation microscopy (see, e.g., Boyer and Lasne),
Stimulated emission microscopy (see, e.g., Min),
Photothermal modulation microscopy (see, e.g., Boyer and Lasne)
1) Coherent interactions with the sample, e.g.,
Stimulated Raman Scattering (SRS) as in Freudiger; an example microscope system for the advantageous application of FMM for SRS is sketched in FIG. 1.
Stimulated fluorescence excitation (see, e.g., Min)
2) Incoherent interactions with the sample, e.g., photothermal imaging (see, e.g., Boyer and Lasne):

Here, normally a "heat beam" of a wavelength 1 is modulated in intensity that then leads, at the focus, to a similarly modulated local change in refractive index around the absorbing structures of the sample. This refractive-index modulation is transmitted to the probe beam of wavelength 2 and detected demodulated (lock-in). Here, the advantage of the proposed method also lies, in turn, in that the entire heat beam 1 does not carry this intensity modulation at each location in the sample, but instead this modulation forms for the first time at the focus. Accordingly, only the contrast-forming, local heating also takes place only in focus; a background signal from other areas is thus avoided. A setup suitable for this arrangement could appear as sketched in FIG. 1 for SRS, but the FMM modulator must now be placed in the pump beam.

For the use of pulsed laser systems (e.g., for SRS), attention must be paid so that the pulse repetition rate is significantly higher than the modulation frequency of the focus modulation (FM), because otherwise the modulation is not adequately scanned (sampled). The pulse rates of the typically used titanium-sapphire laser (e.g., Coherent Chameleon or Spectra Physics MaiTai) lie at 80 MHz; thus a modulation frequency of 1-10 MHz could be used.

DESCRIPTION OF THE EMBODIMENTS

Figure 1:
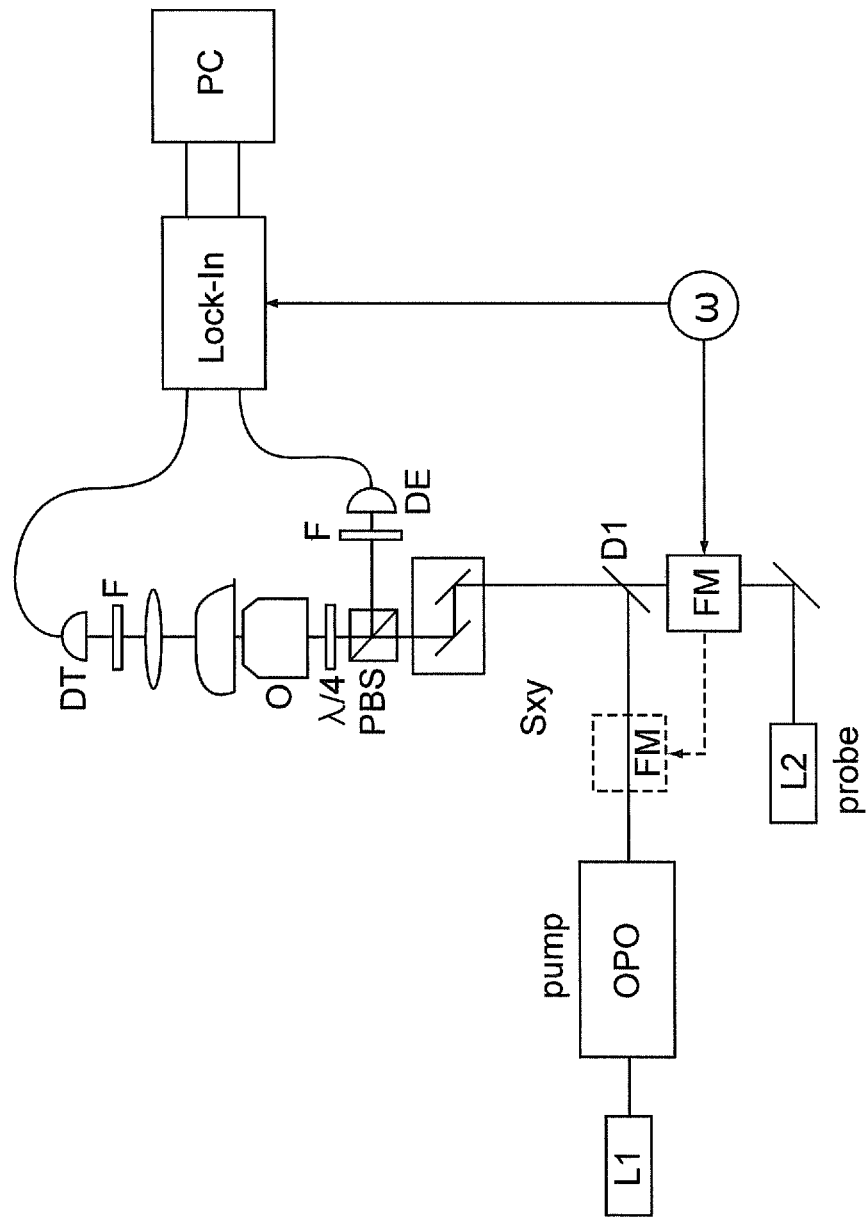
FIG. 1: microscope setup for FMM-SRS microscopy.

FIG. 1 shows, as an embodiment, a microscope system with focus modulator that is suitable for FMM-SRS in transmission or epi-illumination. The focus modulator could be constructed here according to prior art (e.g., Chen and Wong), or advantageously according to FIGS. 3 and 4. Other details are to be inferred in the description of the figures.

Arrangements modified accordingly could be used for the mentioned examples of pump-probe experiments and other comparable experiments.

FIG. 1: example microscope setup for FMM-SRS microscopy. The pump beam is generated by laser L1 and OPO, the probe beam by laser L2.

The Raman signal could be detected either in transmission (detector DT) or in epi-illumination (detector DE). Beam combining is performed by ichroit D1, mirroring of the epi-signal by polarization beam splitter PBS and λ/4 plate. Other components: beam scanner Sxy, demodulation of the signals with lock-in amplifier for modulation frequency.

The focus modulator FM could be positioned either in the probe beam path (as sketched) or in the pump beam path (dashed lines).

Figure 2:
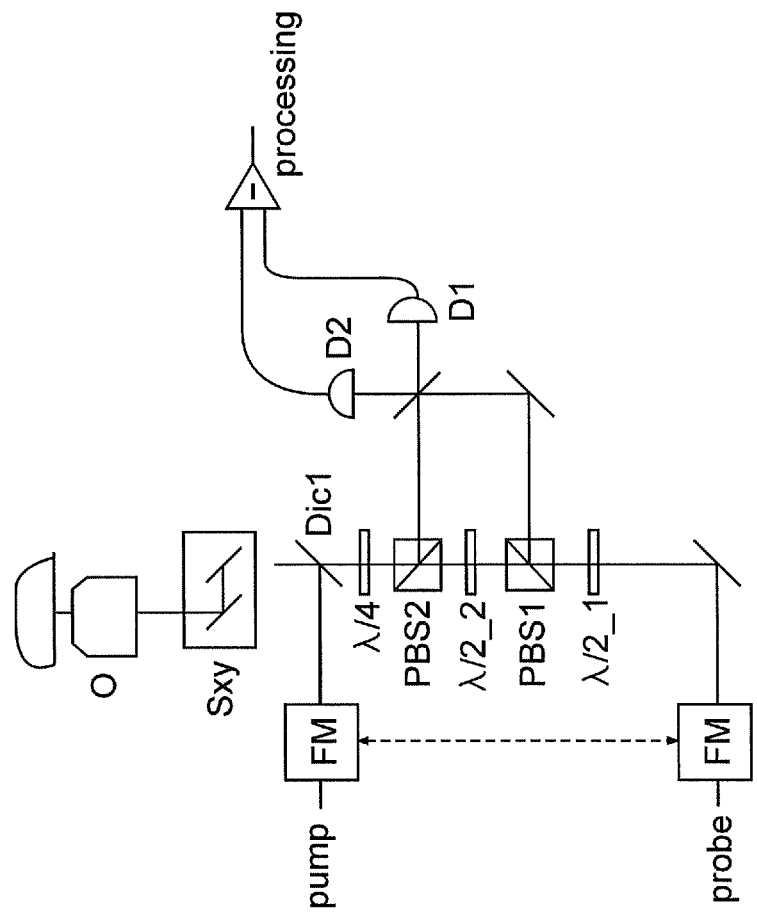
FIG. 2: pump-probe microscope system with focus modulator for epi-illumination in which, in addition to the signal improvement, a balanced detection system is used.

FIG. 2 shows, as an embodiment, a pump-probe microscope system with focus modulator for epi-illumination in which, in addition to the signal improvement, a balanced detection system is used.

For the balanced heterodyne detection, the obtained optical signal is brought into interference with the excitation beam at a 50/50 beam splitter and passed to two detectors. In this way, weak signals can be amplified and common noise sources (e.g., laser noise) can be eliminated by subtraction of the two detector signals.

The relative intensity of the reflected signal beam and the reference beam is set by means of the polarization beam splitters PBS1 and PBS2 in connection with the corresponding λ/2 plates.

Below, particularly advantageous aspects will be explained in more detail with reference to schematic representations of advantageous FMM arrangements in the illumination beam path.

1. Electro-Optical Modulator (EOM):

According to the invention, EOM's are used for especially quick, non-mechanical phase modulation of at least one portion, advantageously half, of the excitation beam.

Advantageously, a portion of the excitation beam could run across the EOM or the EOM could be modulated only partially in a portion in which the excitation beam runs. In an especially advantageous way, different beam sections or halves are modulated differently (opposite phase) by opposite-pole driving of parts of an EOM or by several EOM's.

Electro-optical modulators use the Pockels effect in a double-refractive crystal in which the polarization or phase of the laser light is changed by the application of a voltage. This can take place very quickly depending on the type and size of the crystal (up to a few 10's of MHz).

Below, constructions are described of how this can be used advantageously for FMM microscopy:

EOM crystal with corresponding beam widening and collimated laser beam half illuminated (FIG. 3(a))

EOM crystal in which the electrical alternating field is defined by the electrodes only across the half beam (FIG. 3(b))

EOM with counter-running fields (cf. sequentially arranged, in order to minimize scattering fields) (FIG. 3(c))

Classical EOM in connection with polarizer before and after the beam, wherein only half the beam runs through the polarizers; thus, the intensity of the half beam is modulated directly, which similarly leads to intensity modulation at the focus.

One important basic advantage of all EOM-based solutions is the greatest possible modulation rate of a few 10's of MHz.

Figure 3:
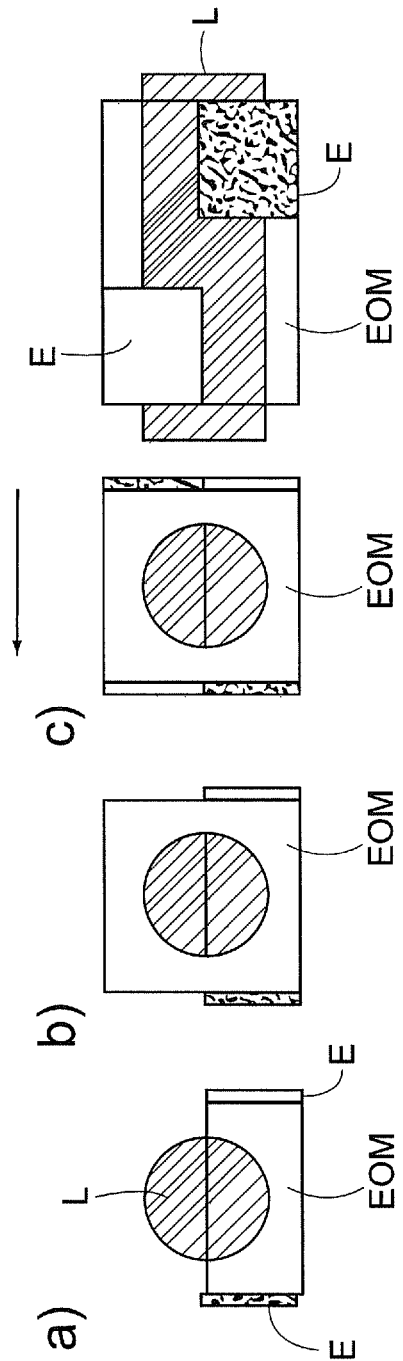
FIG. 3a: Phase modulation of a portion, in particular, of the half laser beam, with an electro-optical modulator. EOM crystal with corresponding beam widening and collimated laser beam half illuminated.
FIG. 3b: EOM crystal in which the electrical alternating field is defined by the electrodes only across the half beam.
FIG. 3c: EOM with counter-running fields.

FIG. 3 shows the phase modulation of a portion, in particular, of the half laser beam, with an electro-optical modulator (EOM).

In FIGS. 3(a) through 3(c), the plane of the EOM is to be seen in a plan view with the laser beam L shown with cross-hatching.

The EOM is positioned in accordance with the teachings of e.g., Chen and Wong, in the illumination beam path, advantageously in a widened (collimated) beam section.

An adaptation of the beam cross section to the crystal size can be realized by the magnitude of the beam widening.

In FIG. 3(a), the modulation space is defined by the EOM by means of an illumination of the crystal with half of the laser beam L.

On the sides, the crystal has electrodes for its high-frequency driving.

In FIG. 3(b), the modulation space is defined by means of the electrodes of the EOM in that only half of the EOM lying across the lower beam half is driven by means of the electrodes, i.e., the crystal is indeed completely illuminated, but only half is modulated (by the position of the electrodes).

In FIG. 3(c), two upper and lower beam halves are modulated differently with electrodes poled with opposite phases in the upper and lower portions.

The modulated sections could, but do not have to be arranged one above the other on the laser beam.

In the right portion in FIG. 3(c), a side view (in the left portion in the direction of the arrow) is shown schematically in which the driven sections are advantageously offset laterally relative to each other.

This could be advantageous for avoiding scattering fields (for EOM, high voltages are required).

An opposite-phase, poled construction could be advantageous, for example, if the crystal is not to be modified, but crosstalk effects from one side to the other are to be avoided. Through the counter-phase driving, the stroke distance (distance of the counter running amplitudes) is also advantageously doubled in comparison with single-phase driving. For a desired phase difference (stroke), the crystal could also be advantageously shortened (shortened running length). Through the offset arrangement of the driven fields of the EOM, overlapping of the two beam fields is also possible (greater than half).

It is interesting that the opposite-phase driving also represents an advantageous refinement of Chen. Here, a second piezo actuator could be installed for the second beam half, wherein both piezo actuators could be operated with opposite phases.

An effect offset along the beam, as shown in FIG. 1(c), is advantageously possible in Chen.

2. Advantageous Use of Acousto-Optical Modulators (AOM) in FMM:

According to the invention, acousto-optical modulators are used in order to modulate the excitation beam in interaction with a splitting into several sub-beam paths and optical elements for the partial phase modulation of the excitation beam and also advantageous actuators for setting the phase difference.

Acousto-optical modulators use the diffraction of the laser beam at a standing sound wave in a crystal for the quick deflection or switching of a laser. This effect could also be used as follows for the quick phase modulation of half the laser beam, if the deflection of the beam is used accordingly:

AOD quickly switches between sub-beam paths each with half, fixed phase shift (e.g., by half glass plate), cf. FIG. 4(a).

AOD quickly switches between sub-beam paths that are re-combined by means of a special beam combiner in which a semicircle is constructed as a mirror and the complementary semicircle is constructed as an aperture (cf. FIG. 4(b)).

The phase shift can be fine adjusted by means of changing the optical path length by means of a piezo actuator at one of the deflection mirrors and thus can be adapted, for example, to different wavelengths.

AOM's do not switch as quickly as EOM's (due to the speed of propagation of sound in the crystal), but are more economical.

With 1-10 MHz, the possible switching rates are still significantly higher than any mechanical or electromechanical elements that can be realized.

Figure 4:
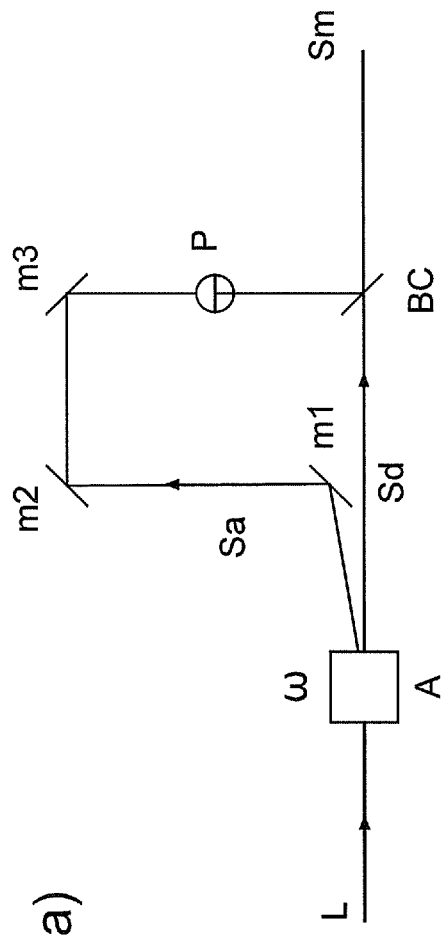
FIG. 4a: Quick phase modulation of half the laser beam L by means of AOM (A), switching is performed between two beam paths, wherein the upper half is guided through the glass plate. The beam paths are re-combined at the beam combiner (BC).
FIG. 4b: As for FIG. 4a, but with a half-mirrored hole mask as the beam combiner (white=mirrored, black=opening).
Figure 4:
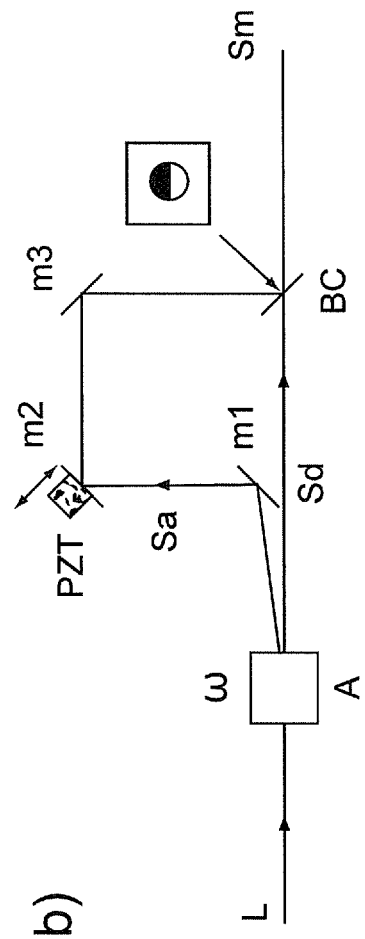

FIG. 4 shows the quick phase modulation of half the laser beam L by means of AOM (A).

In FIG. 4(a), switching is performed between two beam paths, wherein the upper half is guided through the glass plate. The beam paths are re-combined at the beam combiner (BC).

In FIG. 4(b), in part like in FIG. 4(a), but with a half-mirrored hole mask as the beam combiner (white=mirrored, black=opening).

In each part of FIG. 4, a laser beam is shown in the region of the illumination of the microscope, an acousto-optical element A like, for example, an AOM, and deflection mirrors m1, m2, m3, beam combiner BC, and a piezo actuator PZT, as well as a semicircular glass plate P.

A is an acousto-optical deflector and switches a beam at a frequency ω back and forth between two angular directions in which a continuous beam Sd and a deflected beam Sa run, in Sa via mirrors m1, m2, m3 as the beam loop. Plate P in FIG. 4(a) is a glass plate as a semicircle; thus the full beam Sa of the loop is phase modulated on half and the continuous beam is not phase modulated; at the beam combiner BC, the two beams are superimposed again and obtain, in BC, a half modulated beam Sm.

The absolute phase of the upper, bypassed beam can be set by means of a mirror on a piezo actuator (PZT) (slow, DC). The quick modulation is performed by switching between the beam paths through the AOM.

The piezo element PZT in FIG. 4(b) could also be a mirror with a mechanical actuator as indicated in FIG. 4(a) by the arrow, in order to be able to adjust the path difference.

The AOM switches between the two beams with ω and therefore switches the half-beam phase modulation on and off; this then leads at the focus to the intensity modulation according to the invention. This intensity modulation rises and falls periodically but is not necessarily a pure sine function; it could have, e.g., a square profile; this is to be taken into consideration in the demodulation (higher harmonic portions). For a sine function approximated by the AOM, the deflection angle between continuous and deflected beam would be slightly varied by the AOM on M1.

In FIG. 4(b), there is no phase plate in Sa, but instead in BC there is a semicircular, reflective part and an open semicircle (half hole aperture); i.e., the reflective portion is influence phase-shifted across the path length difference of the beam paths (adjustable by the actuator PCT) and after BC, the beam Sm has two phase-shifted halves that are superimposed at the focus.

The modulation method described here could be used together with a quick lock-in amplifier directly for the FMM microscopy discussed as in Chen and Wong.

While the invention has been illustrated and described in connection with currently preferred embodiments shown and described in detail, it is not intended to be limited to the details shown since various modifications and structural changes may be made without departing in any way from the spirit of the present invention. The embodiments were chosen and described in order to best explain the principles of the invention and practical application to thereby enable a person skilled in the art to best utilize the invention and various embodiments with various modifications as are suited to the particular use contemplated.

What is claimed:

1. A microscope comprising at least one light source providing an illumination beam that is phase-modulated along its cross section partially with a temporal modulation frequency for excitation of a sample, an electro-optical modulator EOM located only partially in said illumination beam, said at least one light source being a first light source providing a first beam of a first wavelength for performing local excitation of a transition of said sample, a second light source providing a second beam for inducing said transition, and a detection unit for reading out and detecting said transition.

2. The microscope according to claim 1, wherein the second beam has the same wavelength as said first beam or uses the same beam as said first beam, said first beam and said second beam being used in a time-offset way for short-term spectroscopy.

3. The microscope according to claim 1, wherein different beam sections or halves of the illumination beam are modulated differently, with opposite phases, by opposite-pole driving of portions of one EOM or several EOM' s.

4. The microscope according to claim 1, wherein at least one acousto-optical modulator is provided for splitting said illuminating beam into at least one sub-beam path.

5. The microscope according to claim 4, wherein in at least one beam path there is an optical element for the partial phase modulation of the illumination beam, and further, actuators for setting a phase difference.

6. The microscope of claim 1 wherein the local excitation is a fluorescence excitation in a sample.

7. The microscope of claim 1 wherein the second beam has a different wavelength to the first beam.

8. The microscope of claim 1 wherein the detection unit is an infrared camera.

9. The microscope according to claim 1 further comprising means for coherent pump-probe microscopy.

10. The microscope according to claim 1 further comprising means for incoherent pump-probe microscopy.

11. The microscope according to claim 1 for use in a microscope operating with Induced Raman scattering or Stimulated Raman Scattering (SRS).

12. The microscope according to claim 1 for use in a microscope operating with photothermal modulation microscopy.

13. The microscope according to claim 1, for use in a microscope operating with stimulated emission microscopy.

14. A method for the microscopic detection of light from a sample, comprising illuminating said sample with at least one illumination beam via a microscope objective for focusing said illumination beam, said illumination beam being partially phase-modulated at a temporal modulation frequency in its cross section in a microscope, having an electro-optical modulator (EOM) located only partially in said illumination beam, for performing said illuminating and local excitation of a transition of said sample by means of a first beam of a first wavelength, inducing said transition by means of a second beam, and reading and detecting said transition by means of a detection unit.

15. The method according to claim 14, wherein the second beam has the same wavelength as said first beam or uses the same beam as said first beam, said first and second beams being used in a time-offset way for short-term spectroscopy.

16. The method according to claim 14 further comprising steps for coherent pump-probe microscopy.

17. The method according to claim 14 further comprising steps for incoherent pump-probe microscopy.

18. The method according to claim 14 further comprising steps for Induced Raman scattering or Stimulated Raman Scattering (SRS).

19. The method according to claim 14 further comprising steps for photothermal modulation microscopy.

20. The method according to claim 14 further comprising steps for stimulated emission microscopy.

* * * * *